(12) United States Patent
Horiike

(10) Patent No.: US 12,714,396 B2
(45) Date of Patent: Aug. 25, 2026

(54) DRIVE UNIT, DIAGNOSTIC IMAGING APPARATUS, AND OPERATION METHOD

(71) Applicant: TERUMO KABUSHIKI KAISHA, Tokyo (JP)

(72) Inventor: Toyokazu Horiike, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 150 days.

(21) Appl. No.: 17/956,077

(22) Filed: Sep. 29, 2022

(65) Prior Publication Data

US 2023/0013321 A1 Jan. 19, 2023

Related U.S. Application Data

(63) Continuation of application No. PCT/JP2021/008824, filed on Mar. 5, 2021.

(30) Foreign Application Priority Data

Mar. 30, 2020 (JP) ................................ 2020-061491

(51) Int. Cl.
*A61B 8/00* (2006.01)
*A61B 5/00* (2006.01)
*A61B 8/12* (2006.01)

(52) U.S. Cl.
CPC .............. *A61B 8/4416* (2013.01); *A61B 8/12* (2013.01); *A61B 8/4461* (2013.01); *A61B 8/463* (2013.01);

(Continued)

(58) Field of Classification Search
None
See application file for complete search history.

(56) References Cited

U.S. PATENT DOCUMENTS 6,004,271 A * 12/1999 Moore ................. A61B 8/4209 600/463
2007/0232893 A1* 10/2007 Tanioka ............. A61B 5/02007 600/407

(Continued)

FOREIGN PATENT DOCUMENTS

JP 2013070814 A 4/2013
JP 2015181788 A 10/2015

(Continued)

OTHER PUBLICATIONS

International Search Report (PCT/ISA/210) with translation and Written Opinion (PCT/ISA/237) mailed on May 25, 2021, by the Japanese Patent Office as the International Searching Authority for International Application No. PCT/JP2021/008824. (8 pages).

*Primary Examiner* — Farouk A Bruce
(74) *Attorney, Agent, or Firm* — Buchanan Ingersoll & Rooney PC

(57) ABSTRACT

A drive unit includes: a scanner unit to which a catheter is connectable, an imaging core that executes tomographic imaging and that is positioned in the catheter; and a pull-back unit configured to support the scanner unit such that the scanner unit is displaceable. The drive unit includes a hold unit configured to control a non-hold state in which scanner unit displacement is not restricted and a hold state in which scanner unit displacement is restricted, a driving unit configured to rotationally drive the catheter imaging core, a switching input unit configured to receive a switching input of the hold state and the non-hold state, and a control unit configured to, when a switching input operation from the hold state to the non-hold state is detected while the imaging core is not rotationally driven, rotationally drive the imaging core and then set the scanner unit to the non-hold state.

20 Claims, 6 Drawing Sheets

(52) U.S. Cl.
CPC .......... *A61B 8/5261* (2013.01); *A61B 5/0073* (2013.01); *A61B 5/0084* (2013.01)

(56) References Cited

U.S. PATENT DOCUMENTS

| | | | | |
|---|---|---|---|---|
| 2012/0253185 | A1* | 10/2012 | Furuichi | A61B 8/4461 600/425 |
| 2013/0345676 | A1* | 12/2013 | Wulfman | A61M 25/0147 604/95.01 |
| 2015/0025560 | A1* | 1/2015 | Alhumaid | A61B 17/3468 606/185 |
| 2017/0071568 | A1* | 3/2017 | Mitsuhashi | A61B 8/12 |
| 2020/0121280 | A1 | 4/2020 | Marshall et al. | |

FOREIGN PATENT DOCUMENTS

| | | | |
|---|---|---|---|
| JP | 2018121831 | A | 8/2018 |
| JP | 2018126321 | A | 8/2018 |
| JP | 2018525159 | A | 9/2018 |

* cited by examiner

DRIVE UNIT, DIAGNOSTIC IMAGING APPARATUS, AND OPERATION METHOD

CROSS-REFERENCES TO RELATED APPLICATIONS

This application is a continuation of International Patent Application No. PCT/JP2021/008824 filed on Mar. 5, 2021, which claims priority to Japanese Patent Application No. 2020-061491 filed on Mar. 30, 2020, the entire content of both of which is incorporated herein by reference.

TECHNOLOGICAL FIELD

The present disclosure generally relates to a drive unit, a diagnostic imaging apparatus, and an operation method.

BACKGROUND DISCUSSION

In related art, as an apparatus for diagnosing an intravascular lumen, an intravascular ultrasound (IVUS) diagnostic apparatus, an optical frequency domain imaging (OFDI) apparatus, and the like are known (see, for example, Japanese Patent Application Publication No. 2018-121831).

In the IVUS apparatus, a catheter including an imaging core for measuring a state of an intravascular lumen is connected to a scanner unit of a drive unit, and a motor for displacing a position of the scanner unit is supplied with an electric current to drive the catheter, so that the imaging core can be displaced in a longitudinal direction of the catheter. Some IVUS apparatuses in related art are configured such that supply of current to the motor is stopped and positioning of the imaging core can be executed by manual operation by a user.

However, when the scanner unit is manually displaced, an internal mechanism of the catheter may be damaged. In particular, when an apparatus capable of diagnosing an intravascular lumen by IVUS and OFDI, an optical fiber is provided as the internal mechanism of the catheter, and the optical fiber may be damaged.

SUMMARY

The drive unit, diagnostic imaging apparatus, and operation method disclosed here reduce a possibility that a catheter is damaged by a manual operation.

According to a first aspect of the present disclosure, a drive unit for a diagnostic imaging apparatus includes: a scanner unit to which a catheter, in which is positioned an imaging core that executes tomographic imaging, is connectable; and a pull-back unit that supports the scanner unit such that the scanner unit is displaceable in a predetermined direction. The drive unit includes a hold unit configured to control a non-hold state in which displacement of the scanner unit with respect to the pull-back unit is not restricted and a hold state in which the displacement of the scanner unit with respect to the pull-back unit is restricted, a driving unit configured to rotationally drive the imaging core of the catheter connected to the scanner unit, a switching input unit configured to receive a switching input operation identifying either the hold state or the non-hold state, and a control unit configured to, when there is a detection of the switching input operation performed on the switching input unit from the hold state to the non-hold state while the imaging core is not rotationally driven, rotationally drive the imaging core and then set the scanner unit to the non-hold state.

In the drive unit as one embodiment of the present disclosure, the control unit sets the scanner unit to the hold state when the control unit determines that a state in which the scanner unit is not displaced with respect to the pull-back unit continues for a predetermined time after the scanner unit is set to the non-hold state from the hold state.

The drive unit as one embodiment of the present disclosure further includes a brake unit configured to limit a displacement speed of the scanner unit with respect to the pull-back unit to a predetermined speed or less when the scanner unit is in the non-hold state.

A second aspect of the present disclosure involves a diagnostic imaging apparatus that includes a catheter in which is positioned an imaging core that executes tomographic imaging; a scanner unit to which the catheter is connected; a pull-back unit on which the scanner unit is movably supported for movement in a predetermined direction relative to the pull-back unit; a hold unit configured to control a non-hold state in which displacement of the scanner unit with respect to the pull-back unit is not restricted and a hold state in which the displacement of the scanner unit with respect to the pull-back unit is restricted; a driving unit configured to rotationally drive the imaging core of the catheter connected to the scanner unit; a switching input unit configured to receive a switching input operation identifying either the hold state or the non-hold state; a control unit configured to, upon detecting the switching input operation performed on the switching input unit to change from the hold state to the non-hold state while the imaging core is not rotationally driven, rotationally drive the imaging core and then set the scanner unit to the non-hold state; and an image processing device configured to generate a tomographic image based on a signal acquired by the imaging core executing the tomographic imaging.

In the diagnostic imaging apparatus as one embodiment of the present disclosure, the imaging core is capable of executing tomographic imaging using light and tomographic imaging using ultrasound.

An operation method as a third aspect of the present disclosure is an operation method of a drive unit, the drive unit including a scanner unit to which is connectable a catheter in which is positioned an imaging core that executes tomographic imaging, and a pull-back unit on which the scanner unit is movably supported such that the scanner unit is movable relative to the pull-back unit in a predetermined direction, the drive unit being configured to control a non-hold state in which displacement of the scanner unit with respect to the pull-back unit is not restricted and a hold state in which the displacement of the scanner unit with respect to the pull-back unit is restricted. The operation method includes: detecting a switching input from the hold state to the non-hold state; detecting whether the imaging core is rotationally driven when the switching input is detected; rotationally driving the imaging core when the imaging core is not rotationally driven; and setting the scanner unit to the non-hold state after the imaging core is rotationally driven.

According to the present disclosure, it is possible to provide the drive unit, the diagnostic imaging apparatus, and the operation method capable of reducing the possibility that a catheter is damaged by a manual operation.

DETAILED DESCRIPTION

A diagnostic imaging apparatus according to the present embodiment has an IVUS function and an OFDI function.

1. Appearance Configuration of Diagnostic Imaging Apparatus

Figure 1:
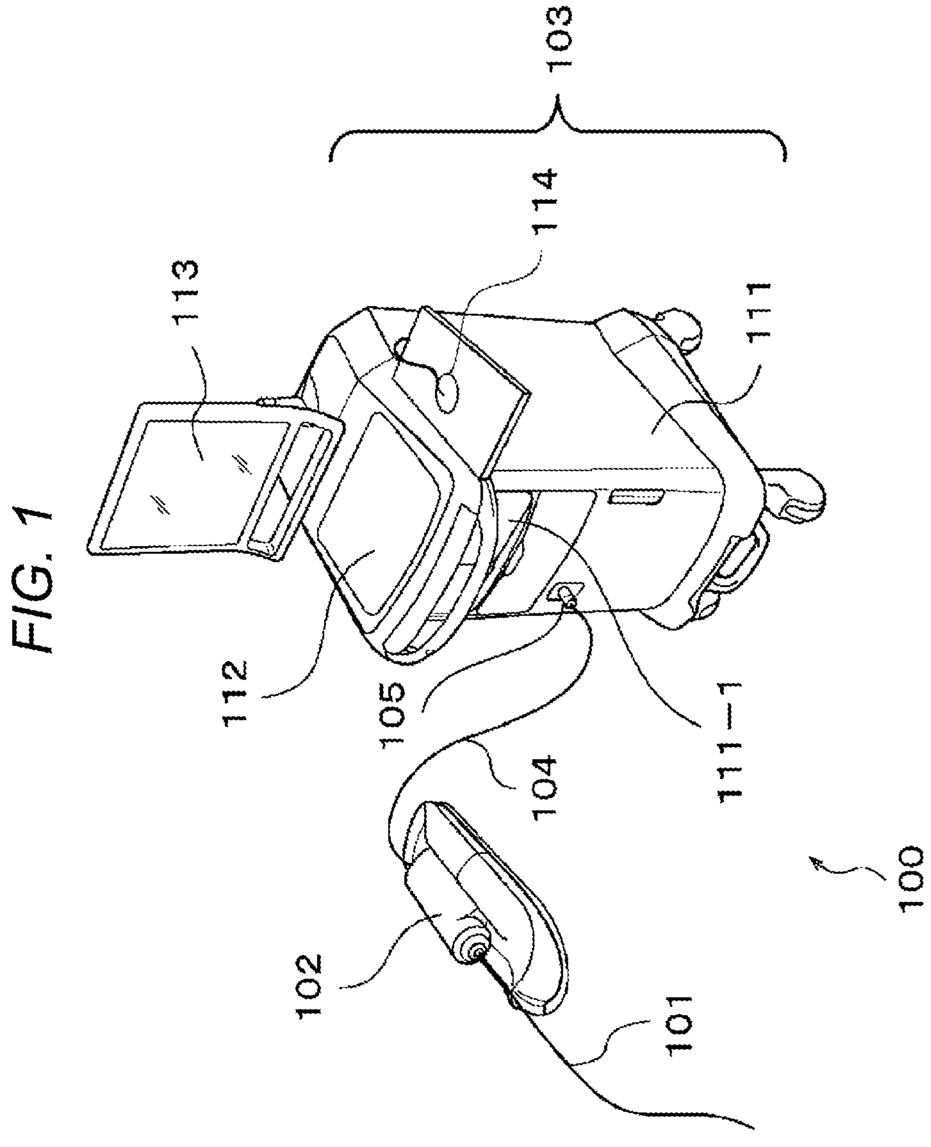
FIG. 1 is a diagram showing an example of an appearance configuration of a diagnostic imaging apparatus.

FIG. 1 is a diagram showing an appearance configuration of a diagnostic imaging apparatus 100 according to an embodiment. As shown in FIG. 1, the diagnostic imaging apparatus 100 includes a catheter 101, a scanner and a pull-back unit (hereinafter, referred to as a motor drive unit (MDU)) 102, an image processing device 103 as a tomographic imaging device, and a display device 113. The MDU 102 is a drive unit in the present disclosure. The MDU 102 and the image processing device 103 are connected to each other via a connector 105 by a cable 104 accommodating a signal line and an optical fiber. In the present embodiment, the image processing device 103 and the display device 113 are described as separate components, but the image processing device 103 may include the display device 113.

The catheter 101 is directly inserted into a blood vessel. The catheter 101 has an imaging core inserted therein, the imaging core including an ultrasound transmitter and receiver that transmits ultrasound based on a pulse signal and receives a reflected wave from an inside of a blood vessel, and an optical transmitter and receiver that continuously transmits transmitted light (measurement light) to the inside of the blood vessel and continuously receives reflected light from the inside of the blood vessel. The diagnostic imaging apparatus 100 measures a state of the inside of a blood vessel (acquires a tomographic image) by using the imaging core. That is, the diagnostic imaging apparatus 100 obtains a tomographic image by blood vessel tomographic imaging based on a return signal of an ultrasound signal from the catheter 101 and an optical interference signal.

The MDU 102, to which the catheter 101 is detachably attached, regulates an axial motion in a major axis (axial) direction in a blood vessel and a rotational motion of the imaging core inserted into the catheter 101 by driving a built-in motor. In addition, the MDU 102 acquires a signal of the reflected wave received by the ultrasound transmitter and receiver in the imaging core and a signal of the reflected light received by the optical transmitter and receiver, and transmits the signals to the image processing device 103.

The image processing device 103 has a function of inputting various setting values when performing measurement, and a function of processing ultrasound data and optical interference data obtained by the measurement and displaying various blood vessel images.

The image processing device 103 includes a main control unit 111. The main control unit 111 generates line data from the signal of the reflected wave of the ultrasound obtained by the measurement, and generates an ultrasound tomographic image of the blood vessel (IVUS image) through interpolation processing. Further, the main control unit 111 generates interference light data by causing the reflected light from the imaging core and reference light obtained by separating light from a light source to interfere with each other, generates the line data based on the interference light data, and generates an optical tomographic image of the blood vessels (OFDI image) through the interpolation processing.

The main control unit 111 includes a printer and a DVD recorder 111-1. The printer and the DVD recorder 111-1 prints a processing result in the main control unit 111 or stores the processing result as data. The main control unit 111 further includes an operation panel 112. A user inputs various setting values and instructions using the operation panel 112. The display device 113 includes, for example, an LCD monitor, and displays various cross-sectional images generated by the main control unit 111. The main control unit 111 further includes a mouse 114 as a pointing device (coordinate input device), and can perform an operation performed on the operation panel 112 on a screen of the LCD monitor.

2. Functional Configuration of Diagnostic Imaging Apparatus (Mainly Image Processing Device)

Figure 2:
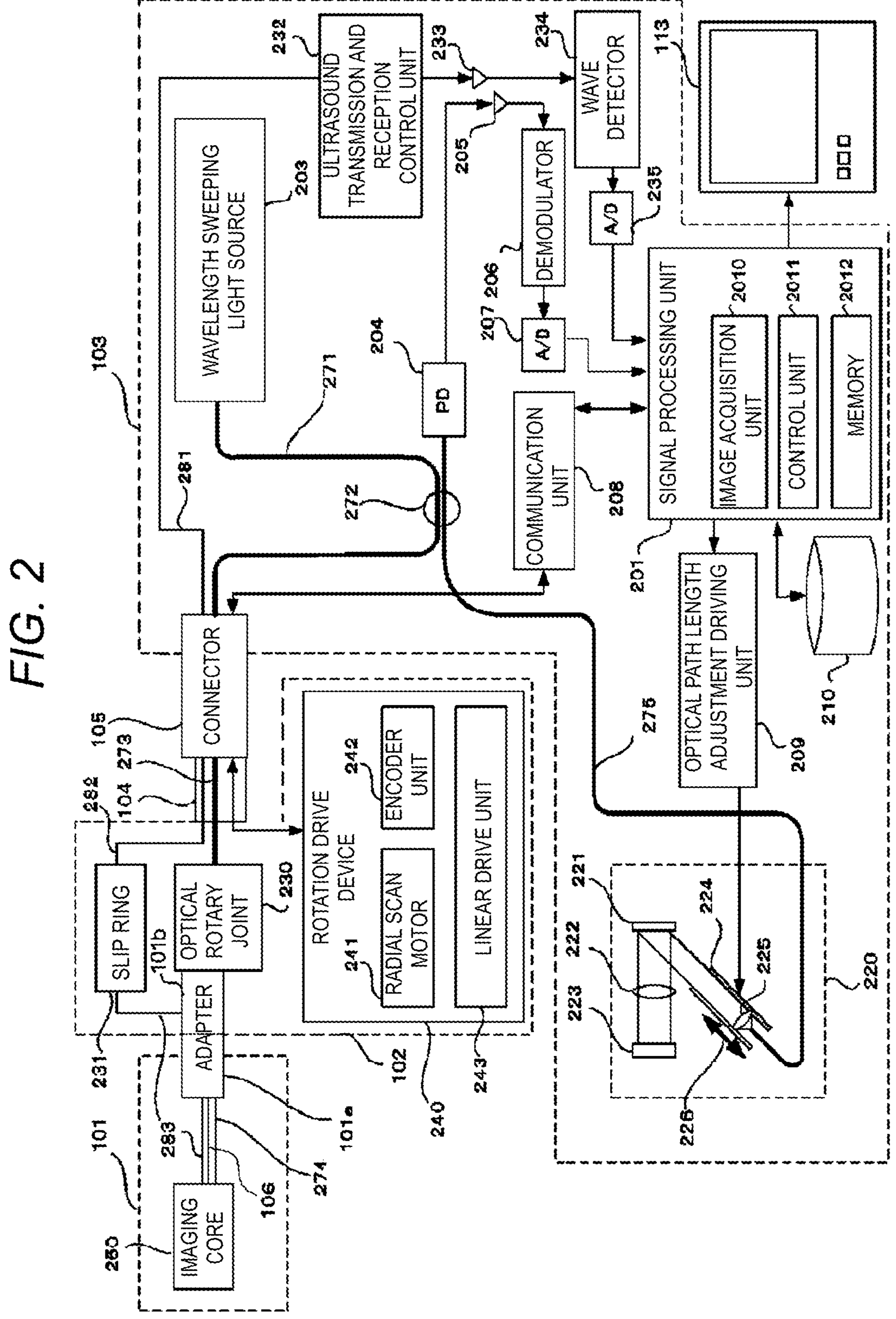
FIG. 2 is a block diagram showing a configuration example of the diagnostic imaging apparatus.

Next, a functional configuration of the diagnostic imaging apparatus 100 (mainly, the image processing device 103) will be described. FIG. 2 is a block diagram showing a configuration example of the diagnostic imaging apparatus 100. Hereinafter, a functional configuration for implementing wavelength-sweeping optical coherence tomographic imaging (OFDI) and ultrasound tomographic imaging (IVUS) will be described with reference to FIG. 2.

In FIG. 2, the image processing device 103 includes a signal processing unit 201 that controls the entire diagnostic imaging apparatus 100. The signal processing unit 201 is formed of several circuits including a microprocessor. For example, the signal processing unit 201 includes an image acquisition unit 2010. The image acquisition unit 2010 acquires an ultrasound tomographic image (IVUS image) or an optical coherence tomography image (OFDI image) captured by an imaging core 250 to be described later. The signal processing unit 201 further includes a control unit 2011. The control unit 2011 performs various processes and controls display on the display device 113. The signal processing unit 201 further includes a memory 2012. The memory 2012 includes, for example, a random access memory (RAM). The image processing device 103 further includes a storage device 210. The storage device 210 is a nonvolatile storage device represented by a hard disk, and stores various programs to be executed by the signal processing unit 201 and data files.

The image processing device 103 includes a wavelength sweeping light source 203. The wavelength sweeping light source 203 is a light source that repeatedly generates light of a wavelength that changes within a preset range along a time axis. The light output from the wavelength sweeping light source 203 enters one end of a first single mode fiber 271 and transmits toward a distal end side. The first single mode fiber 271 is optically coupled to a fourth single mode fiber 275 at an optical fiber coupler 272 in the middle.

The light entering the first single mode fiber 271 and emitted to the distal end side from the optical fiber coupler 272 is guided to a second single mode fiber 273 via the connector 105. The other end of the second single mode fiber 273 is connected to an optical rotary joint 230 in the MDU 102.

Meanwhile, the catheter 101 includes an adapter 101*a* for connecting to the MDU 102. In addition, the MDU 102 includes an adapter 101*b* for connecting to the catheter 101. By attaching the adapter 101*a* to the adapter 101*b*, the catheter 101 and the MDU 102 are connected to each other, and the catheter 101 is stably held by the MDU 102. The catheter 101 further includes a shaft 106 connected to the imaging core 250 and connected to the catheter 101. The shaft 106 transmits a rotational motion caused by the MDU 102 around a longitudinal direction of the imaging core 250. That is, when the catheter 101 is connected to the MDU 102, the rotational motion caused or produced by the MDU 102 is transmitted to the shaft 106, so that the imaging core 250 is rotationally driven.

An end portion of a third single mode fiber 274 rotatably accommodated in the catheter 101 is connected to the optical rotary joint 230. As a result, the second single mode fiber 273 and the third single mode fiber 274 are optically coupled. On the other end of the third single mode fiber 274 (on a side of a leading portion of the catheter 101), the imaging core 250 is provided, on which the optical transmitter and receiver is mounted, the optical transmitter and receiver including a mirror and a lens for emitting light in a direction substantially orthogonal to a rotation axis.

As a result, the light emitted from the wavelength sweeping light source 203 is guided to the imaging core 250 provided at the end portion of the third single mode fiber 274 via the first single mode fiber 271, the second single mode fiber 273, and the third single mode fiber 274 as optical fibers. The optical transmitter and receiver of the imaging core 250 emits the light in a direction orthogonal to an axis of the fiber and receives the reflected light, and the received reflected light is reversely guided this time and returned to the image processing device 103.

Meanwhile, an optical path length adjusting mechanism 220 for finely adjusting an optical path length of the reference light is provided at an end portion of the fourth single mode fiber 275 that is opposite to an end portion coupled to the optical fiber coupler 272. The optical path length adjusting mechanism 220 functions as an optical path length changing unit that changes the optical path length corresponding to a variation in the length of the catheter 101 so as to be capable of absorbing the variation in the length of each catheter 101, when, for example, the catheter 101 is replaced. Therefore, a collimating lens 225 positioned at an end portion of the fourth single mode fiber 275 is provided on an one-axis stage 224 that can be moved in an optical axis direction of the collimating lens 225 as indicated by an arrow 226.

Specifically, when the catheter 101 is replaced, the one-axis stage 224 functions as the optical path length changing unit having a variable range of the optical path length that can absorb the variation in the optical path length of the catheter 101. Further, the one-axis stage 224 also has a function as an adjusting unit for adjusting offset. For example, even when a distal end of the catheter 101 is not in close contact with a surface of biological tissue, it is possible to set a state in which the distal end of the catheter 101 interferes with a reflected light from a surface position of the biological tissue by the one-axis stage 224 slightly changing the optical path length.

The optical path length is finely adjusted by the one-axis stage 224, and light reflected by a mirror 223 is guided again to the fourth single mode fiber 275 via a grating 221 and a lens 222, mixed with the light obtained from a second single mode fiber 273 side by the optical fiber coupler 272, and received by a photodiode 204 as interference light.

The interference light received by the photodiode 204 in this manner is photoelectrically converted, amplified by an amplifier 205, and then input to a demodulator 206. The demodulator 206 performs demodulation processing for extracting only a signal portion of the interfered light, and an output thereof is input to an A/D converter 207 as an interference light signal.

The A/D converter 207 samples the interference light signal at, for example, 90 MHz for 2048 points to generate digital data (interference light data) of one line. A sampling frequency of 90 MHz is based on a premise that when a repetition frequency of wavelength sweeping is 40 kHz, about 90% of a cycle (25 μsec) of the wavelength sweeping is extracted as the digital data of 2048 points, and is not particularly limited thereto.

The interference light data in a line unit generated by the A/D converter 207 is input to the signal processing unit 201 and temporarily stored in the memory 2012. Then, the signal processing unit 201 generates data in a depth direction (line data) by performing frequency resolution on the interference light data by fast fourier transform (FFT), constructs an optical tomographic image at each position in the blood vessel by performing coordinate transformation on the data, and outputs the optical tomographic image to the display device 113 at a predetermined frame rate.

The signal processing unit 201 is further connected to an optical path length adjustment driving unit 209 and a communication unit 208. The signal processing unit 201 controls a position of the one-axis stage 224 (optical path length control) via the optical path length adjustment driving unit 209.

The communication unit 208 incorporates several drive circuits and communicates with the MDU 102 under the control of the signal processing unit 201. Specifically, the communication unit 208 communicates with a radial scan motor 241, an encoder unit 242, and a linear drive unit 243 included in a rotation drive device 240 via the connector 105. More specifically, the communication unit 208 supplies a drive signal to the radial scan motor 241 for rotating the third single mode fiber 274 by the optical rotary joint in the MDU 102, receives a signal from the encoder unit 242 for detecting a rotational position of the radial scan motor 241, and supplies a drive signal to the linear drive unit 243 for pulling the third single mode fiber 274 at a predetermined speed.

The above processing in the signal processing unit 201 is implemented by a computer executing a predetermined program.

When optical interference scanning is executed by the diagnostic imaging apparatus 100 having the above configuration, the catheter 101 is positioned at a blood vessel position (coronary artery or the like) of a patient to be diagnosed, and a transparent flush liquid is discharged into a blood vessel through a guiding catheter or the like toward the distal end of the catheter 101 by an operation of a user. This is to exclude an influence of blood. When the user inputs an instruction to start the scanning, the signal processing unit 201 drives the wavelength sweeping light source 203 to drive the radial scan motor 241 and the linear drive unit 243 (hereinafter, light emission and light reception processing performed by driving the radial scan motor 241 and the linear drive unit 243 are referred to as scanning). As a result, wavelength sweeping light from the wavelength sweeping light source 203 is supplied to the imaging core 250 through the above-described path. At this time, since the imaging core 250 at a distal end position of the catheter 101 moves along a rotation axis while rotating, the imaging core 250 emits light to an intravascular lumen surface and receives reflected light thereof while rotating and moving along a blood vessel axis.

Next, a configuration according to image formation using ultrasound and processing contents thereof will be described. Scanning using ultrasound is performed simultaneously with the optical interference scanning described above. That is, when scanning is performed and the imaging core 250 is moved in a catheter sheath of the catheter 101 while rotating the imaging core 250, emission of ultrasound and detection of a reflected wave thereof from the ultrasound transmitter and receiver accommodated in the imaging core 250 are performed. For this reason, the diagnostic imaging apparatus 100 needs to generate a drive signal for driving the ultrasound transmitter and receiver accommodated in the imaging core 250, and to receive a detection signal of the ultrasound output from the ultrasound transmitter and receiver. Transmission of the drive signal and the reception of the detection signal are executed by an ultrasound transmission and reception control unit 232. The ultrasound transmission and reception control unit 232 and the imaging core 250 are connected to each other via signal line cables 281, 282, 283. Since the imaging core 250 rotates, the signal line cables 282, 283 are electrically connected to each other via a slip ring 231 provided in the MDU 102. Although the signal line cables 281 to 283 are shown as being connected by one line in FIG. 2, a plurality of signal lines may be accommodated in practice.

The ultrasound transmission and reception control unit 232 operates under the control of the signal processing unit 201, drives the ultrasound transmitter and receiver accommodated in the imaging core 250, and cause the ultrasound transmitter and receiver to generate a pulse wave of ultrasound. The ultrasound transmitter and receiver converts a reflected wave from vascular tissue into an electric signal, and supplies the electric signal to the ultrasound transmission and reception control unit 232. The ultrasound transmission and reception control unit 232 outputs the received ultrasound signal to an amplifier 233. The amplifier 233 amplifies the ultrasound signal. The amplified ultrasound signal is supplied to the signal processing unit 201 as ultrasound data via a wave detector 234 and an A/D converter 235, and is temporarily stored in the memory 2012. The A/D converter 235 samples the ultrasound signal output from the wave detector 234 at, for example, 30.6 MHz for 200 points to generate digital data (ultrasound data) of one line. Although 30.6 MHz is used here, this is calculated based on a premise that the sampling for 200 points is performed with respect to a depth of 5 mm when a sound velocity is 1530 m/sec. Therefore, the sampling frequency is not particularly limited thereto.

The signal processing unit 201 converts the ultrasound data stored in the memory 202 into a gray scale to generate an ultrasound image for each position in the blood vessel.

Figure 3:
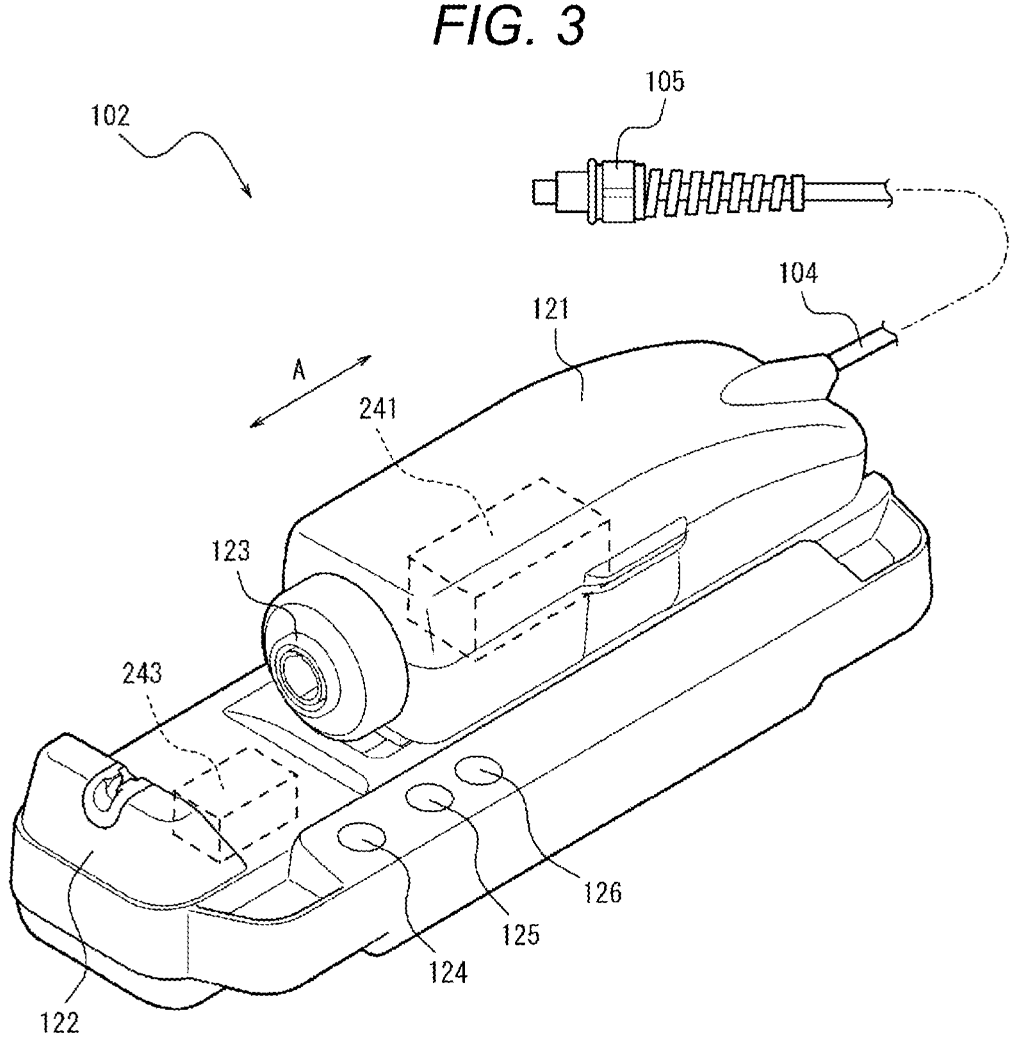
FIG. 3 is a diagram showing an example of an appearance configuration of a motor drive unit or an MDU in FIG. 1.

FIG. 3 is a diagram showing an example of an appearance configuration of the MDU 102 in FIG. 1, and is a diagram showing an example of the appearance configuration more detailed than that in FIG. 1. The MDU 102 includes a scanner unit 121 and a pull-back unit 122. As shown in FIG. 3, the scanner unit 121 is supported (placed) by the pull-back unit 122. The scanner unit 121 is displaceable in a predetermined direction on the pull-back unit 122. Specifically, the scanner unit 121 is displaceable in one direction with respect to the pull-back unit 122, and in the present embodiment, is displaceable in a direction A indicated by an arrow in FIG. 3.

The scanner unit 121 includes a catheter connecting portion 123 to which the catheter 101 can be connected (detached). The catheter connecting portion 123 is provided on one end side of the scanner unit 121 in one direction (that is, the direction indicated by the arrow in FIG. 3) in which the catheter connecting portion 123 is displaceable.

In the scanner unit 121, the cable 104 is connected to the other end side which is a side opposite to the one end side, and the connector 105 is connected to a distal end of the cable 104. When the connector 105 is connected to the image processing device 103, the scanner unit 121 can communicate information with the image processing device 103 via the cable 104.

The scanner unit 121 includes the radial scan motor 241 therein. The radial scan motor 241 is an example of a driving unit in the present disclosure. The radial scan motor 241 is a motor that rotationally drives the imaging core 250 inserted into or positioned in the catheter 101 connected to the catheter connecting portion 123 of the scanner unit 121 based on control of a control unit 127 to be described later.

The pull-back unit 122 includes an input unit that receives an input operation by the user. In the example shown in FIG. 3, the pull-back unit 122 includes a switching input unit 124, a scan input unit 125, and a pull-back input unit 126 as the input units. In the present embodiment, all of the switching input unit 124, the scan input unit 125, and the pull-back input unit 126 may be implemented as operation buttons (operation keys) that can be pressed. However, the form of the input unit is not limited to the operation buttons that can be pressed. The input unit may include, for example, a touch screen, and may display an input region for receiving an operation input from the user on a part of the display device to receive a touch operation input by the user. The input units are not necessarily the switching input unit 124, the scan input unit 125, and the pull-back input unit 126. The MDU 102 may include an input unit for an appropriate mode, quantity, and arrangement according to a function that can be executed by the MDU 102.

The switching input unit 124 is a button for switching the scanner unit 121 between a hold state and a non-hold state. The hold state and the non-hold state will be described later. The scan input unit 125 is a button for causing the diagnostic imaging apparatus 100 to execute scanning. The pull-back input unit 126 is a button for causing the MDU 102 to execute pull-back. The pull-back is to displace or move the scanner unit 121 supported by the pull-back unit 122 in one direction with respect to the pull-back unit 122 by driving the linear drive unit 243 including a motor or the like. In the present embodiment, the pull-back means that the scanner unit 121 is displaced from one end side to the other end side.

Figure 4:
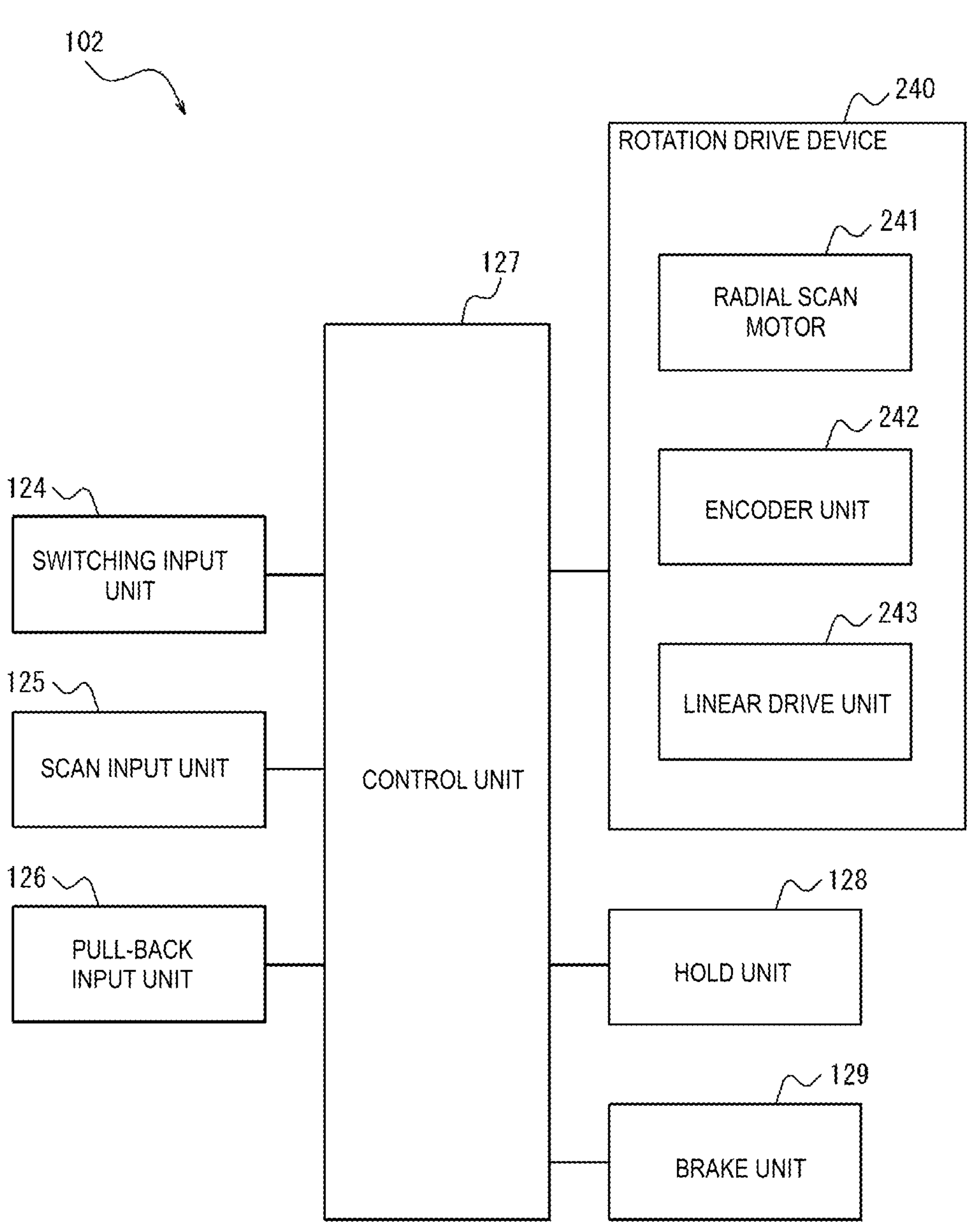
FIG. 4 is a functional block diagram showing a schematic configuration of the MDU in FIG. 1.

FIG. 4 is a functional block diagram showing a schematic configuration of the MDU 102. As shown in FIG. 4, the MDU 102 includes, as functional blocks, the control unit 127, a hold unit 128, a brake unit 129, the switching input unit 124, the scan input unit 125, the pull-back input unit 126, and the rotation drive device 240. Since the switching input unit 124, the scan input unit 125, the pull-back input unit 126, and the rotation drive device 240 are as described above, detailed description thereof will be omitted here. The rotation drive device 240 includes the radial scan motor 241, the encoder unit 242, and the linear drive unit 243.

The control unit 127 controls and manages the entire MDU 102 including functional units of the MDU 102. The control unit 127 includes at least one processor. The control unit 127 is formed by a processor such as a central processing unit (CPU) that executes a program defining a control procedure or a dedicated processor specialized for processing of each function. Such a program is stored in a storage unit (not shown) included in the MDU 102 or a storage medium external to the MDU 102.

The control unit 127 performs various control based on an input operation performed on the input unit by the user. In the present embodiment, the control unit 127 performs a switching process between the hold state and the non-hold state by the hold unit 128 based on an input operation performed on the switching input unit 124 by the user. The switching process executed by the control unit 127 will be described in detail later.

The hold unit 128 switches between the hold state and the non-hold state under the control of the control unit 127.

Here, the hold state is a state in which the displacement of the scanner unit 121 with respect to the pull-back unit 122 is restricted. The state in which the displacement is restricted refers to a state in which a positional relationship with respect to the pull-back unit 122 does not change even when a hand or the like attempts to move the scanner unit 121. That is, in the hold state, a position of the scanner unit 121 with respect to the pull-back unit 122 is fixed. However, when the input operation performed on the scan input unit 125 and the pull-back input unit 126 as the input units is received, by driving the radial scan motor 241 or the linear drive unit 243, the control unit 127 can displace or move the scanner unit 121 even in the hold state by the pull-back unit 122. Therefore, the hold state refers to a state in which the user cannot freely displace the scanner unit 121 with respect to the pull-back unit 122. (the user cannot manually displace or move the scanner unit 121 with respect to the pull-back unit 122).

On the other hand, the non-hold state is a state in which the displacement of the scanner unit 121 with respect to the pull-back unit 122 is not restricted. Therefore, in the non-hold state, the user can displace the scanner unit 121 with respect to the pull-back unit 122 by a hand or the like (the user can manually displace or move the scanner unit 121 with respect to the pull-back unit 122).

The hold unit 128 may have any configuration capable of restricting the displacement of the scanner unit 121 with respect to the pull-back unit 122. For example, the hold unit 128 may be implemented by a mechanism capable of locking the scanner unit 121 with respect to the pull-back unit 122 by mechanically sandwiching the scanner unit 121. Alternatively, the hold unit 128 may be implemented by a mechanism capable of locking the scanner unit 121 with respect to the pull-back unit 122 by electromagnetic locking using an electromagnet, for example. As an example, the hold unit 128 may restrict the displacement of the scanner unit 121 by an excitation force of the motor included in the linear drive unit 243. In this case, when the hold unit 128 causes a current to flow through the motor included in the linear drive unit 243, the motor is excited, and a shaft of the motor does not rotate. As a result, the displacement of the scanner unit 121 can be restricted.

When the scanner unit 121 is in the non-hold state, the brake unit 129 limits a displacement speed of the scanner unit 121 with respect to the pull-back unit 122 to a predetermined speed or less. The brake unit 129 can be implemented by a known mechanism such as a disc brake or an eddy-current brake.

For example, when the displacement speed of the scanner unit 121 with respect to the pull-back unit 122 exceeds the predetermined speed, the brake unit 129 may stop the displacement of the scanner unit 121, or may control the displacement speed of the scanner unit 121 with respect to the pull-back unit 122, so that the displacement speed does not exceed the predetermined speed. The predetermined speed is preferably less than 70 mm/sec, and more preferably less than 40 mm/sec. This is because when the predetermined speed is less than 70 mm/sec, the shaft 106 can easily follow the displacement of the scanner unit 121, and when the predetermined speed is less than 40 mm/sec, the shaft 106 can more reliably follow the displacement of the scanner unit 121.

The brake unit 129 may be configured to operate only when the scanner unit 121 is displaced from the other end side where the cable 104 is provided toward the one end side where the catheter connecting portion 123 is provided. As will be described later, displacing the scanner unit 121 from the other end side to the one end side may cause disconnection in an internal mechanism of the catheter 101. Therefore, by limiting the displacement speed with respect to at least the displacement of the scanner unit 121 from the other end side to the one end side, it is possible to reduce a possibility that the internal mechanism of the catheter 101 is damaged.

In the diagnostic imaging apparatus 100, the user can move the scanner unit 121 with respect to the pull-back unit 122 by a hand or the like by setting the scanner unit 121 to the non-hold state. For example, a position of the imaging core 250 can be adjusted or determined by moving the scanner unit 121 in a state where the catheter 101 is connected to the MDU 102. However, when the imaging core 250 is moved in the longitudinal direction of the catheter 101 by moving the scanner unit 121 without rotating the internal mechanism of the catheter 101, the internal mechanism of the catheter 101 may be damaged. For example, when the scanner unit 121 is moved in a state where the shaft 106 is bent in the catheter 101, there is a possibility that a twist occurs in an optical fiber (that is, the third single mode fiber 274) or the like, which is the internal mechanism of the catheter 101, and disconnection occurs. In particular, when the scanner unit 121 is displaced from the other end side where the cable 104 is provided toward the one end side where the catheter connecting portion 123 is provided, a degree of the twist increases, and the possibility of disconnection increases.

On the other hand, when the imaging core 250 is moved in the longitudinal direction of the catheter 101 in a state where the internal mechanism of the catheter 101 is rotationally driven, it is possible to reduce the possibility that the internal mechanism such as the optical fiber is damaged. Therefore, in the present embodiment, the control unit 127 sets the scanner unit 121 to the non-hold state in a mode in which the internal mechanism of the catheter 101 is not easily damaged. Specifically, when a switching input operation from the hold state to the non-hold state is detected, in a case where the imaging core 250 is not rotationally driven, the control unit 127 rotationally drives the imaging core 250, and sets the scanner unit 121 to the non-hold state in the state where the imaging core 250 is rotationally driven.

Figure 5:
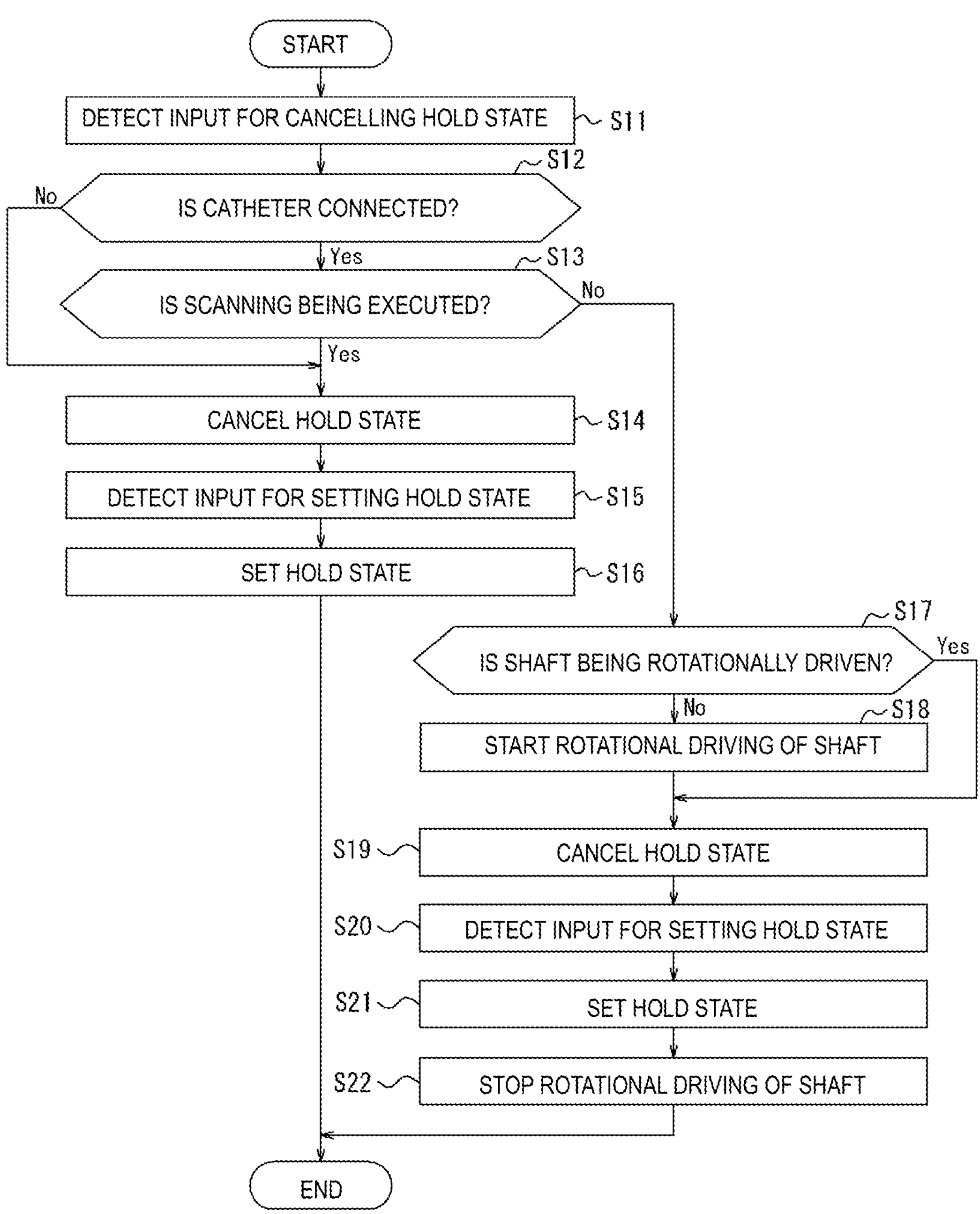
FIG. 5 is a flowchart showing an example of a switching process executed by a control unit in FIG. 4.

Here, details of the switching process between the hold state and the non-hold state executed by the control unit 127 will be described with reference to FIG. 5. FIG. 5 is a flowchart showing an example of the switching process executed by the control unit 127. At a start of FIG. 5, it is assumed that the scanner unit 121 is in the hold state.

First, the user presses the switching input unit 124 in order to switch the scanner unit 121 from the hold state to the non-hold state. Then, the control unit 127 detects that cancellation of the hold state is input by pressing the switching input unit 124 (step S11).

Then, the control unit 127 determines whether the catheter 101 is connected to the scanner unit 121 (step S12). The control unit 127 can detect whether the catheter 101 is connected to the scanner unit 121 by any known method.

The control unit 127 can detect whether the catheter 101 is connected to the scanner unit 121 by, for example, an electrical or mechanical method. Specifically, for example, a protrusion may be provided in the adapter 101*a* of the catheter 101, and when the catheter 101 is connected to the scanner unit 121, a microswitch provided in the catheter connecting portion 123 may be pressed by the protrusion. In this case, when the microswitch is pressed, it is possible to detect that the catheter 101 is connected to the scanner unit 121. However, the method of detecting whether the catheter 101 is connected to the scanner unit 121 is not limited thereto, and any other method can be adopted.

When the control unit 127 determines that the catheter 101 is not connected to the scanner unit 121 (No in step S12), the control unit 127 cancels the hold state of the scanner unit 121 (step S14). That is, the control unit 127 switches the scanner unit 121 from the hold state to the non-hold state. This is because, when the catheter 101 is not connected to the scanner unit 121, the internal mechanism of the catheter 101 is not damaged even when the user moves the scanner unit 121 in the predetermined direction by a hand or the like (manually moves the scanner 121).

In this case, the user presses the switching input unit 124 again in order to switch the scanner unit 121 from the non-hold state to the hold state. The control unit 127 detects that a setting of the hold state is input by pressing the switching input unit 124 (step S15).

In response to the input of the setting of the hold state in step S15, the control unit 127 sets the hold state (step S16). That is, the control unit 127 switches the scanner unit 121 from the non-hold state to the hold state.

On the other hand, when the control unit 127 determines in step S12 that the catheter 101 is connected to the scanner unit 121 (Yes in step S12), the control unit 127 detects whether the MDU 102 is executing scanning (step S13). The control unit 127 can determine whether the scanning is being executed based on whether scanning processing is being performed.

When the control unit 127 determines that the MDU 102 is executing the scanning (Yes in step S13), the control unit 127 cancels the hold state of the scanner unit 121 (step S14). That is, the control unit 127 switches the scanner unit 121 from the hold state to the non-hold state. This is because, when the MDU 102 is executing the scanning, the radial scan motor 241 is driven and the imaging core 250 is rotationally driven, and thus, even when the hold state is cancelled, the internal mechanism of the catheter 101 is less likely to be damaged.

In this case, the user presses the switching input unit 124 again in order to switch the scanner unit 121 from the non-hold state to the hold state. The control unit 127 detects that a setting of the hold state is input by pressing the switching input unit 124 (step S15).

In response to the input of the setting of the hold state in step S15, the control unit 127 sets the hold state (step S16). That is, the control unit 127 switches the scanner unit 121 from the non-hold state to the hold state. At this time, the control unit 127 may cause the MDU 102 to continuously execute the scanning. That is, the state in which the radial scan motor 241 is driven may be maintained. As a result, the scanning can be continued.

On the other hand, when the control unit 127 determines in step S13 that the MDU 102 is not executing the scanning (No in step S13), the control unit 127 determines whether the shaft 106 is rotationally driven (step S17). The control unit 127 can determine whether the shaft 106 is rotationally driven based on whether the radial scan motor 241 is driven.

When the control unit 127 determines that the shaft 106 is rotationally driven (Yes in step S17), the process proceeds to step S19.

On the other hand, when the control unit 127 determines that the shaft 106 is not rotationally driven (No in step S17), the control unit 127 starts the rotational motion of the shaft 106 (step S18). Specifically, the control unit 127 starts the rotational motion of the shaft 106 by driving the radial scan motor 241. As a result, the imaging core 250 is rotationally driven.

Then, the control unit 127 cancels the hold state of the scanner unit 121 (step S19). That is, the control unit 127 switches the scanner unit 121 from the hold state to the non-hold state. As a result, the user can move the scanner unit 121 in the predetermined direction by a hand or the like (the user can manually move the scanner unit 121). At this time, since the imaging core 250 is in a state of being rotationally driven by the rotational driving of the shaft 106, the hold state is cancelled in a state where the possibility that the internal mechanism of the catheter 101 is damaged is reduced. This makes it easy to maintain safety of the diagnostic imaging apparatus 100.

The user presses the switching input unit 124 again in order to switch the scanner unit 121 from the non-hold state to the hold state. The control unit 127 detects that a setting of the hold state is input by pressing the switching input unit 124 (step S20).

In response to the input of the setting of the hold state in step S20, the control unit 127 sets the hold state (step S21). That is, the control unit 127 switches the scanner unit 121 from the non-hold state to the hold state.

In addition, the control unit 127 stops the rotational driving of the shaft 106 (step S22). Specifically, the control unit 127 stops the rotational motion of the shaft 106 by stopping the radial scan motor 241. In this manner, when the scanning is not executed, the control unit 127 can stop the rotational motion of the shaft 106 when switching the non-hold state to the hold state.

When the scanning is not executed (No in Step S13) and the shaft 106 is rotationally driven (Yes in Step S17), the control unit 127 may not stop the rotational motion of the shaft 106 when the hold state is set again after the hold state is cancelled once. That is, in this case, step S22 may not be executed. Accordingly, when the hold state is set again after the hold state is cancelled once, the hold state can be returned to the same state as that before the hold state is cancelled.

Figure 6:
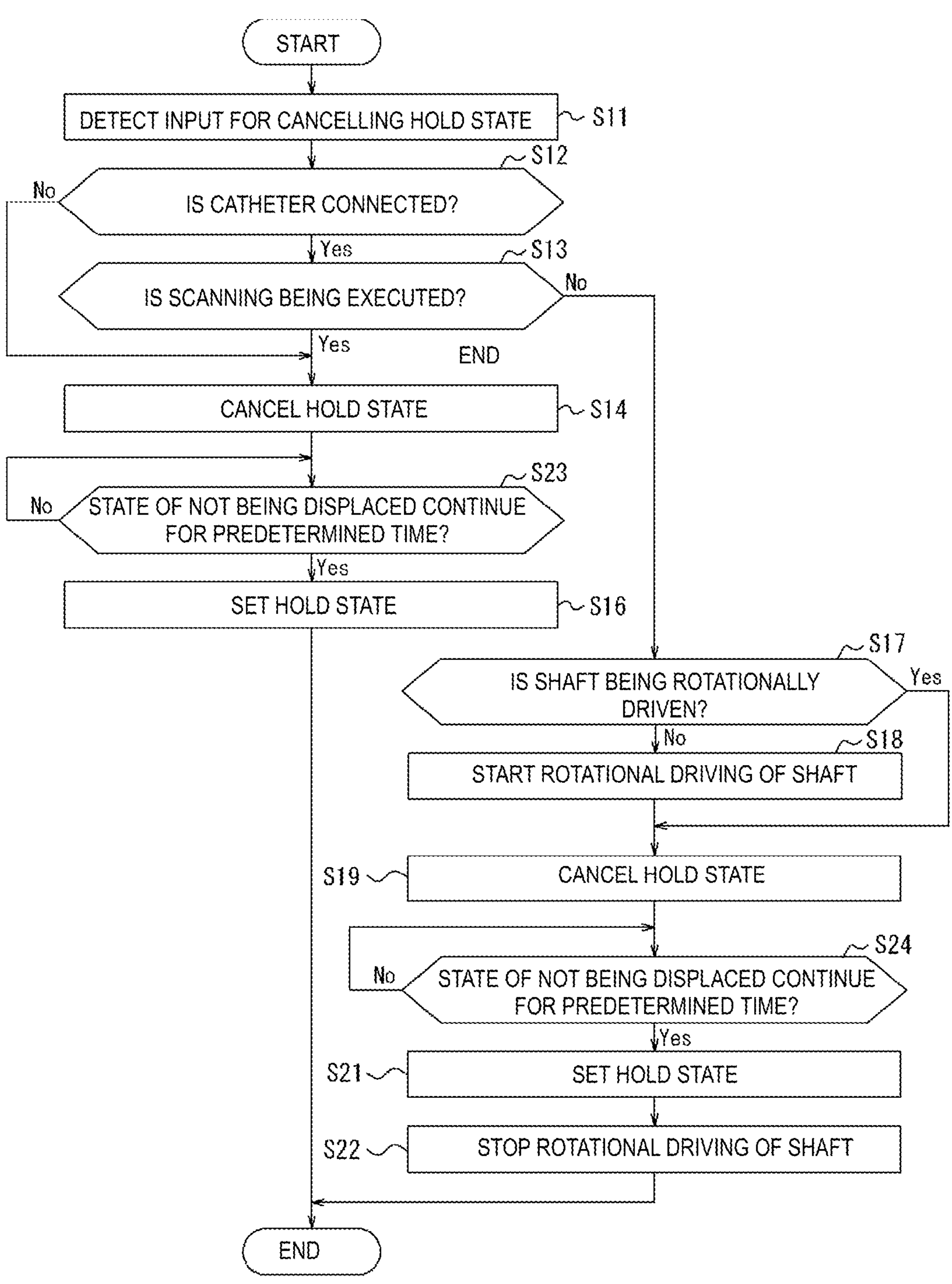
FIG. 6 is a flowchart showing another example of the switching process executed by the control unit in FIG. 4.

The control unit 127 may not necessarily execute the switching process in the procedure shown in FIG. 5. FIG. 6 is a flowchart showing another example of the switching process executed by the control unit 127.

In the flow shown in FIG. 6, steps S11 to S14 are the same as steps S11 to S14 described in FIG. 5, respectively, and thus detailed description thereof will be omitted here.

After the hold state is cancelled in step S14, the control unit 127 determines whether a state where the scanner unit 121 is not displaced with respect to the pull-back unit 122 continues for a predetermined time (step S23). The predetermined time is a time at which it is estimated that the user does not intend to displace or move the scanner unit 121 by a hand or the like, and is appropriately determined. For example, the predetermined time can be set to a time of several tens of seconds to several minutes.

When the control unit 127 determines that the state where the scanner unit 121 is not displaced with respect to the pull-back unit 122 does not continue for the predetermined time (No in step S23), the control unit 127 repeats step S23.

When the control unit 127 determines that the state where the scanner unit 121 is not displaced with respect to the pull-back unit 122 continues for the predetermined time (Yes in step S23), the control unit 127 sets the hold state (step S16).

Similarly, in the flow shown in FIG. 6, steps S17 to S19 are the same as steps S17 to S19 described in FIG. 5, respectively, and thus detailed description thereof will be omitted here.

After the hold state is cancelled in step S19, the control unit 127 determines whether a state where the scanner unit 121 is not displaced with respect to the pull-back unit 122 continues for a predetermined time (step S24). The predetermined time is a time at which it is estimated that the user does not intend to displace or move the scanner unit 121 by a hand or the like, and is appropriately determined. The predetermined time in step S24 may be the same as or different from the predetermined time in step S23.

When the control unit 127 determines that the state where the scanner unit 121 is not displaced with respect to the pull-back unit 122 does not continue for the predetermined time (No in step S24), the control unit 127 repeats step S24.

When the control unit 127 determines that the state where the scanner unit 121 is not displaced with respect to the pull-back unit 122 continues for the predetermined time (Yes in step S24), the control unit 127 sets the hold state (step S21) and stops the rotational driving of the shaft 106 (step S22).

By setting the hold state when the state where the scanner unit 121 is not displaced continues for the predetermined time as in steps S23 and S24, the non-hold state can be automatically switched to the hold state when it is estimated that the user does not intend to move or displace the scanner unit 121 by a hand or the like (does not intend to manually move the scanner unit 121). As a result, it is possible to reduce a possibility that the hold state is maintained for a long period of time and the scanner unit 121 is unintentionally displaced.

The control unit 127 may switch the non-hold state to the hold state by combining the flows shown in FIGS. 5 and 6. That is, after the hold state is cancelled and the hold state is switched to the non-hold state, the control unit 127 may switch the non-hold state to the hold state when the input of the setting of the hold state by the user is detected or when the state where the scanner unit 121 is not displaced continues for the predetermined time.

As described above, according to the diagnostic imaging apparatus 100 of the present embodiment, when the switching input operation from the hold state to the non-hold state is detected, in the case where the imaging core 250 is not rotationally driven, the control unit 127 rotationally drives the imaging core 250 and then sets the scanner unit 121 to the non-hold state. Therefore, the hold state can be cancelled (switched to the non-hold state) in the state where the possibility that the internal mechanism of the catheter 101 is damaged is reduced.

In the above embodiment, in the case where the imaging core 250 is not rotationally driven, the scanner unit 121 is set to the non-hold state after the imaging core 250 is rotationally driven. However, the switching process performed by the control unit 127 is not limited thereto. For example, when the control unit 127 detects the input for cancelling the hold state in step S11 of FIGS. 5 and 6, even when the control unit 127 determines that the scanning is being executed (Yes in step S13) or the shaft 106 is rotationally driven (Yes in step S17), the control unit 127 may increase a rotation speed of the shaft 106 to a predetermined rotation speed and then cancel the hold state when the rotation speed of the shaft 106 is equal to or less than the predetermined rotation speed. The predetermined rotation speed may be a rotation speed at which damage of the internal mechanism of the catheter 101 can be reduced to a predetermined degree. Therefore, it is possible to more reliably reduce the possibility of the damage when the hold state is cancelled.

The detailed description above describes embodiments of a drive unit, a diagnostic imaging apparatus, and an operation method representing examples of the drive unit, diagnostic imaging apparatus, and method of operation disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A drive unit for a diagnostic imaging apparatus, the drive unit comprising:
- a scanner unit to which a catheter, in which is positioned an imaging core that executes tomographic imaging, is connectable;
- a pull-back unit that supports the scanner unit such that the scanner unit is displaceable in a predetermined direction relative to the pull-back unit;
- a hold unit configured to control a non-hold state in which displacement of the scanner unit with respect to the pull-back unit is not restricted and a hold state in which the displacement of the scanner unit with respect to the pull-back unit is fixed by an electromagnetic locking of the scanner unit with respect to the pull-back unit;
- a driving unit configured to rotationally drive the imaging core of the catheter connected to the scanner unit;
- a switching input unit configured to receive a switching input operation identifying either the hold state or the non-hold state;
- a scan input unit configured to cause the diagnostic imaging apparatus to execute scanning;
- a pull-back input unit configured to cause the driving unit to execute pull-back; and
- a control unit configured to, when there is a detection of the switching input operation performed on the switching input unit from the hold state to the non-hold state while the imaging core is not rotationally driven, rotationally drive the imaging core and then set the scanner unit to the non-hold state, and when there is a detection of an input operation performed on one or more of the scan input unit and the pull-back input unit in the hold state, displace or move the scanner unit with respect to the pull-back unit.

2. The drive unit according to claim 1, wherein the control unit sets the scanner unit to the hold state when the control unit determines that a state in which the scanner unit is not displaced with respect to the pull-back unit continues for a predetermined time after the scanner unit is set to the non-hold state from the hold state.

3. The drive unit according to claim 1, further comprising:
- a brake unit configured to limit a displacement speed of the scanner unit with respect to the pull-back unit to a predetermined speed or less when the scanner unit is in the non-hold state.

4. The drive unit according to claim 1, wherein the driving unit is a radial scan motor.

5. The drive unit according to claim 1, wherein one end of the scanner unit in the predetermined direction includes a catheter connecting portion to which the catheter is connectable, and a cable having one end connected to the scanner unit at an end of the scanner unit opposite the one end; and an end of the cable opposite the one end of the cable is connected to a connector that is configured to be connected to an image processing device.

6. An operation method of the drive unit of claim 1, the operation method comprising:

detecting a switching input indicating a switch from the hold state to the non-hold state;

detecting whether the imaging core is rotationally driven when the switching input is detected;

rotationally driving the imaging core when the imaging core is not rotationally driven; and setting the scanner unit to the non-hold state after the imaging core is rotationally driven.

7. The operation method according to claim 6, wherein the switching input is a first switching input, the operation method further comprising:

detecting a second switching input indicating a switch from the non-hold state to the hold state after the setting of the scanner unit to the non-hold state;

setting the scanner unit to the non-hold state after the imaging core is rotationally driven;

stopping the rotational driving of the imaging core.

8. The operation method according to claim 6, further comprising:

detecting whether the catheter is connected to the scanner unit and whether scanning is being performed by the scanner unit after the detecting of the switching input indicating the switch from the hold state to the non-hold state; and the detecting of whether the imaging core is rotationally driven occurring after detecting that the catheter is connected to the scanner unit and that the scanning is being performed by the scanner unit.

9. The operation method according to claim 6, further comprising:

after setting the scanner unit to the non-hold state, determining that a state in which the scanner unit is not displaced with respect to the pull-back unit continues for a predetermined time after the scanner unit is set to the non-hold state from the hold state; and setting the scanner unit to the hold state when it is determined that the state in which the scanner unit is not displaced with respect to the pull-back unit continues for the predetermined time after the scanner unit is set to the non-hold state.

10. The operation method according to claim 6, further comprising:

limiting a displacement speed of the scanner unit with respect to the pull-back unit to a predetermined speed or less when the scanner unit is in the non-hold state.

11. The drive unit according to claim 1, wherein the electromagnetic locking of the scanner unit with respect to the pull-back unit comprises:

an electromagnet that induces an excitation force in a linear drive unit of the motor, which excites the motor and restricts the displacement of the scanner unit.

12. A diagnostic imaging apparatus comprising:

a catheter in which is positioned an imaging core that executes tomographic imaging;

a scanner unit to which the catheter is connected;

a pull-back unit on which the scanner unit is movably supported for movement in a predetermined direction relative to the pull-back unit;

a hold unit configured to control a non-hold state in which displacement of the scanner unit with respect to the pull-back unit is not restricted and a hold state in which the displacement of the scanner unit with respect to the pull-back unit is fixed by an electromagnetic locking of the scanner unit with respect to the pull-back unit;

a driving unit configured to rotationally drive the imaging core of the catheter connected to the scanner unit;

a switching input unit configured to receive a switching input operation identifying either the hold state or the non-hold state;

a scan input unit configured to cause the diagnostic imaging apparatus to execute scanning;

a pull-back input unit configured to cause the driving unit to execute pull-back;

a control unit configured to, upon detecting the switching input operation performed on the switching input unit to change from the hold state to the non-hold state while the imaging core is not rotationally driven, rotationally drive the imaging core and then set the scanner unit to the non-hold state, and upon detecting an input operation performed on one or more of the scan input unit and the pull-back input unit in the hold state, displace or move the scanner unit with respect to the pull-back unit; and an image processing device configured to generate a tomographic image based on a signal acquired by the imaging core executing the tomographic imaging.

13. The diagnostic imaging apparatus according to claim 12, wherein the imaging core is configured to execute both tomographic imaging using light and tomographic imaging using ultrasound.

14. The diagnostic imaging apparatus according to claim 12, further comprising:

a display connected to the image processing device to display the tomographic images.

15. The diagnostic imaging apparatus according to claim 14, wherein the display and the image processing device are separate components.

16. The diagnostic imaging apparatus according to claim 12, wherein the control unit sets the scanner unit to the hold state when the control unit determines that a state in which the scanner unit is not displaced with respect to the pull-back unit continues for a predetermined time after the scanner unit is set to the non-hold state from the hold state.

17. The diagnostic imaging apparatus according to claim 12, further comprising:

a brake unit configured to limit a displacement speed of the scanner unit with respect to the pull-back unit to a predetermined speed or less when the scanner unit is in the non-hold state.

18. The diagnostic imaging apparatus according to claim 12, wherein the driving unit is a radial scan motor.

19. The diagnostic imaging apparatus according to claim 12, wherein one end of the scanner unit in the predetermined direction includes a catheter connecting portion to which the catheter is connected, and a cable having one end connected to the scanner unit at an end of the scanner unit opposite the one end.

20. The diagnostic imaging apparatus according to claim 12, wherein an end of the cable opposite the one end of the cable is connected to a connector that is configured to be connected to the image processing device.

* * * * *